United States Patent [19]

Gidley et al.

[11] Patent Number: 5,738,897
[45] Date of Patent: Apr. 14, 1998

US005738897A

[54] SUSPENSIONS OF GELLED BIOPOLYMERS

[75] Inventors: Michael John Gidley, Raunds; Nicholas David Hedges, Towcester, both of United Kingdom

[73] Assignee: Quest International B.V., Naarden, Netherlands

[21] Appl. No.: 640,875

[22] PCT Filed: Nov. 2, 1994

[86] PCT No.: PCT/EP94/03611

§ 371 Date: May 1, 1996

§ 102(e) Date: May 1, 1996

[87] PCT Pub. No.: WO95/12988

PCT Pub. Date: May 18, 1995

[30] Foreign Application Priority Data

Nov. 8, 1993 [EP] European Pat. Off. ............. 93308914

[51] Int. Cl.$^6$ ........................................................ A23L 1/05
[52] U.S. Cl. .................. 426/573; 426/574; 426/575; 426/576; 426/577; 424/401
[58] Field of Search ........................... 426/573, 574, 426/575, 576, 577, 578; 127/38; 106/160.1, 205.01; 424/401; 514/844, 847

[56] References Cited

U.S. PATENT DOCUMENTS

| | | | |
|---|---|---|---|
| 4,571,346 | 2/1986 | Lehmann et al. | 426/576 |
| 4,588,602 | 5/1986 | Brown et al. | 426/576 |
| 4,663,178 | 5/1987 | Gehrig et al. | 426/583 |
| 5,424,088 | 6/1995 | Christianson et al. | 426/578 |

FOREIGN PATENT DOCUMENTS

| | | |
|---|---|---|
| 355 908 | 2/1990 | European Pat. Off. |
| 25 50 423 | 5/1976 | Germany. |

OTHER PUBLICATIONS

Database WPI, Week 8340, Derwent Publications Ltd., London, GB; AN 83–779408 & JP,A, 58 142 936, (Morinaga) Aug. 25, 1983 see abstract.

Database WPI, Week 8834, Derwent Publications Ltd., London, GB;, AN 88–237971 & JP,A3 169 948 (SANE) Jul. 13, 1988 see abstract.

*Primary Examiner*—Donald E. Czaja
*Assistant Examiner*—Steven B. Leavitt
*Attorney, Agent, or Firm*—Cushman Darby & Cushman IP Group Pillsbury & Madison Sutro LLP

[57] ABSTRACT

Suspensions of hydrated gelled biopolymer particles obtainable by hydrating dry biopolymer particles at a temperature below $T_{gel}$. Such suspensions may be used in food products such as edible spreads and ice creams or in personal care products such as skin creams and moisturizers, to impart a fatty-like character to the product.

11 Claims, No Drawings

SUSPENSIONS OF GELLED BIOPOLYMERS

This application claims benefit of International application PCT/EP94/03611, filed Nov. 2, 1994.

BACKGROUND OF THE INVENTION

(1) Field of the Invention

The present invention relates to suspensions of gelled and hydrated biopolymer particles as well as to a process for obtaining such suspensions, either from dried gelling biopolymers or from dissolved gelling biopolymers.

(2) Description of the Related Art

It is widely known that gelled biopolymer particles having a specific size when dispersed or suspended in an aqueous medium may have useful properties such as imparting fat-like feel or character to products such as edible spreads and ice creams, but also to personal care products like skin creams and moisturizers. This is for example disclosed in EP 0 355 908 (A). Such biopolymer particles are prepared from the gels which are sheared, shredded or otherwise subjected to shear. In EP 0 501 758 (A) for example it is disclosed that a preformed gel is sheared or shredded. It is also possible to simultaneously form the gel phase and apply shear to the biopolymer, as is disclosed in EP 0 355 908 (A). A considerable disadvantage of these methods is that first a gel state has to be induced by cooling a solution containing said biopolymer, whereafter the gel is sheared either during its formation or following setting, under controlled circumstances to yield the desired particles.

Another disadvantage of these known methods for preparing a suspension of gelled biopolymers particles is that the preparation is carried out in a "wet" state, i.e. there is no active ingredient which can be isolated in a dry state (e.g. as a compact, dry powder or mix) which would be easy to store, handle, transport, sell, etcetera and which upon mixing with a (polar) liquid such as water directly yields the desired suspension or dispersion. The material according to EP-A-0 501 758 always contains from 72 to 99.9 percent water, which makes it a bulky material having considerable disadvantages on storage, transport, handling etcetera.

Suspensions of gelled hydrated biopolymers can be used as fat replacers or fat simulating material to replace fat or oil partially or completely in food products. Another use for the suspensions is in products for personal care, like (skin-) moisturizers, skin creams, ointments, hair gels etcetera. For the purpose of this invention, such suspensions are hereinafter collectively referred to as a fat simulating material, although its application is not limited to food products but includes personal care products such as skin creams, moisturizers or hair gels.

In view of the disadvantages as set out above, there is a need for a convenient, easy to prepare fat simulating material obtainable without the need to first prepare a wet gel which thereafter needs to be sheared under controlled circumstances. Also, there is a need for such a material of which the active ingredient can be isolated in a dry state, thus yielding a compact, dry powder or mix which is ready to use conveniently at any time, and which, upon simple mixing with water or another polar solvent yields a fat simulating material.

SUMMARY OF THE INVENTION

It has now been found that these objectives above can be met by a suspension of particles, which particles comprise hydrated gelled biopolymers, which suspension is obtainable by hydrating dry particles of said biopolymers at a temperature of below $T_{gel}$, under the condition that dry particles are obtained by dehydrating at a temperature of equal to or above $T_{gel}$ a solution comprising at least one biopolymer selected from the group consisting of agar, carrageenan, gelatin, gellan, furcelleran, alginate and (low methoxy) pectin. For the purpose of the invention, the term "hydrating" means: mixing of dry particles with a liquid to obtain completely wetted particles which are thereby swelled to the extent that individual particles can still be identified (using suitable means, e.g. by microscopic observation) and that thus no complete dissolution of the particle material takes place. Due to swelling, an increase in mean size of preferably at least a factor 2 is obtained. Hydration is preferably carried out with a polar liquid, which preferably comprises water. More preferably, the suspended swelled particles thus obtained have a size which is between 2 and 30 times larger than their size in dry state.

For most purposes, it will be preferred that 80% by weight of the suspended biopolymer particles has a mean size below 100 μm.

Biopolymers which can be used to prepare the suspensions according to the invention are selected from the group consisting of agar, carrageenan, gelatin, gellan, furcelleran, alginate, (low methoxy) pectin and mixtures comprising or more of these biopolymers.

DESCRIPTION OF PREFERRED EMBODIMENTS $T_{gel}$ is herein to be understood as the temperature at which, upon cooling, an aqueous solution of the biopolymer concerned, sets to a gel. Of course a gel can only be formed under gelling conditions. Such gelling conditions may be different for the various biopolymers concerned but for each of them known in the art. For example, low methoxy pectin requires that a certain amount of calcium ions is present in the solution from which the gel is to be formed. Under normal conditions and using tap water, this may be the case without the addition of extra calcium ions. However, since the amount of calcium ions may influence $T_{gel}$, it may be desired for some purposes to increase or decrease the amount of calcium ions present in ways known in the art such as by adding sequestrants for removing $Ca^{2+}$. Similarly, carrageenan requires that a certain amount of metal ions like potassium, sodium and/or calcium ions are present in the aqueous solution in which the gel is to be achieved. Therefore, potassium-, sodium- or other metal salt ions may be added intentionally in the form of a solution at any stage of the process of preparation of the gel.

Dry particles which can be used for the preparation of a suspension according to the invention may be obtained by dehydrating at a temperature of equal to or above $T_{gel}$ a solution comprising at least one biopolymer selected from the group consisting of agar, carrageenan, gelatin, gellan, furcelleran, alginate and (low methoxy) pectin. Dehydration can be carried out in a number of ways known in the art, including roller drying and spray drying, but since it is needed that the biopolymer is obtained in a particulate form, a preferred way of drying is spray drying.

For specific purposes, it may be preferred to mix the dry particles comprising the biopolymers as defined above with an additional hydrocolloid (like e.g. xanthan, guar gum, locust bean gum or modified celluloses) and/or a starch-derivative (such as maltodextrin). This can be done by either simple mixing of the dry ingredients or by co-drying (e.g. co-spray-drying) a solution of the biopolymers with the additional compound.

An integrated process for the preparation of a suspension according to the invention, starting from a solution of at least one (gellable) biopolymer selected from the group consisting of agar, carrageenan (kappa- and iota-), gelatin, gellan, furcelleran, alginate and (low methoxy) pectin) may comprise the following steps:
  a. drying the solution at a temperature of at least $T_{gel}$, followed by or simultaneously with
  b. particulation of the dry material, followed by
  c. hydrating the obtained particles with a polar liquid at a temperature lower than $T_{gel}$.

Preferably, step a. and b. are carried out simultaneously, which can be achieved by e.g. spray drying the solution comprising the biopolymer.

For preparing a fat simulating material any suitable biopolymer may be used depending on the specific application, as long as the biopolymers used are capable of forming a gel. Examples of such biopolymers are: carrageenan, gelatin, gellan, furcelleran, alginate, pectin or mixtures thereof. The specific application and the type of biopolymer may also determine the amount of particles needed to achieve the desired properties of a fat simulating material. Amounts may range up to 15% (by dry weight) of particles, calculated on the total amount of suspension.

Depending on the end-use of the suspensions according to the invention they may further comprise components like flavours, fragrances, colours, vitamins, salts, sugars, sugar alcohols, UV-absorbers, emulsifiers or other adjuncts.

The suspensions according to the invention may be used in a food product or personal care product, for example in order to partially or completely replace fat of animal or vegetable origin which would be normally present therein.

The suspensions according to the invention can be may be used to replace all or a portion of the fat, oil or cream in food products like ice cream, yoghurt, salad dressings, mayonnaise, cream, cream cheeses, other cheeses, sour cream, sauces, icings, whipped toppings, frozen confections, milk, coffee whiteners and spreads. The suspension according to the invention can also be used in personal care products.

The invention is illustrated by the following examples but is in no way limited thereto.

EXAMPLE 1

By co-spray drying at a temperature T above $T_{gel}$ three samples of agar containing particles were prepared. The obtained particles contained the following ingredients:

| no: | composition: | ratio (weight): |
| --- | --- | --- |
| 1 | agar + maltodextrin | 1:4 |
| 2 | agar + maltodextrin + xanthan | 1:3:0.05 |
| 3 | agar + maltodextrin + xanthan | 1:3:0.1 |

The agar used in all experiments was: Biogar (ex Quest International). The maltodextrin used in all experiments was: Paselli SA2 (ex Avebe). The xanthan used in all experiments was: Jungbunzlauer food-grade xanthan.

A conventional spray-drier was used having the following diameters: total chamber height is 1.8 meters, the top cylindrical section having a diameter of 1.3 meters and a height of 1.0 meters with the conical section being at an angle of 60° for 0.8 meters from the cylinder. Inlet temperature of the spray-drier was 190° C., outlet temperature about 90° C. Feed rate was 9 l. per hour. The agar concentration was about 3.5% by weight and does not include the other ingredients. A spinning disc-type atomizer was used for particulation.

The particle sizes of the dried powders were obtained using a Quantimet 970 Image Analyser. The powders were spread over a microscope slide which was sonicated in order to obtain, as best as possible, discrete particles. It should be noted that the image analysis routine in the Quantimet ignores large, irregular shaped particles in determining particles sizes, i.e. particles that have clumped together. The results of the obtained particle size measurements of the dry particles are set out in table 1.

TABLE 1 particle size distribution dry agar particles (cumulative mean diameters)

| upper limit (μm) | no. 1 | no. 2 | no. 3 |
| --- | --- | --- | --- |
| 5.0 | 22.28 | 29.57 | 29.25 |
| 7.5 | 59.69 | 68.78 | 65.73 |
| 10.0 | 82.28 | 87.85 | 81.81 |
| 12.5 | 92.35 | 95.46 | 90.68 |
| 15.0 | 96.79 | 98.20 | 94.50 |
| 17.5 | 98.70 | 99.26 | 97.27 |
| 20.0 | 99.60 | 99.63 | 98.67 |
| 22.5 | 99.84 | 99.83 | 99.48 |
| 25.0 | 99.98 | 99.88 | 99.86 |
| 27.5 | 100.00 | 100.00 | 100.00 |

EXAMPLE 2

The particles were dispersed or suspended in water in the following manner:
  1. dried agar powder as obtained by spray drying according to the previous example (1 g) was gradually dispersed in cold water (100 ml) using an Ultraturrax T25 Homogeniser with a 16N probe (speed setting 8000 rpm).
  2. Once the powder was fully dispersed the homogenisation speed was increased to 24000 rpm for 2–3 minutes.
  3. The thus obtained particles were left to equilibrate for at least 1 hour before being measured. The obtained mix appeared to be translucent.

Image analysis on the resulting suspensions was not possible using the Quantimet, due to the similarity between the particle and solvent refractive indices. In order to determine the particle size of the dispersed particles a Malvern Mastersizer X was employed. The results are set out in table 2.

TABLE 2 particle size distribution suspended agar particles (cumulative mean diameters)

| upper limit (μm) | no. 1 | no. 2 | no. 3 |
| --- | --- | --- | --- |
| 5.24 | 0.03 | 0.0 | 0.0 |
| 7.78 | 0.33 | 0.08 | 0.11 |
| 11.55 | 1.69 | 1.51 | 1.42 |
| 17.15 | 9.82 | 11.16 | 9.93 |
| 25.46 | 31.57 | 34.03 | 30.91 |
| 37.79 | 65.44 | 62.80 | 59.11 |
| 56.09 | 90.85 | 84.16 | 81.32 |
| 83.26 | 97.79 | 93.24 | 91.14 |
| 123.59 | 97.81 | 96.22 | 94.66 |
| 183.44 | 98.14 | 98.27 | 97.45 |
| 272.31 | 99.37 | 99.69 | 99.49 |
| 404.21 | 100.00 | 100.00 | 100.00 |

EXAMPLE 3

Kappa-carrageenan particles were dispersed or suspended in water in the following manner:

1. dried kappa-carrageenan (ex Quest International, tradename Deltagel) powder as obtained by spray drying similarly to example 1 (1 g) was gradually dispersed in cold water (100 ml) containing 0.015 M KCl using an Ultraturrax T25 Homogeniser with a 16N probe (speed setting 8000 rpm).
2. Once the powder was fully dispersed the homogenisation speed was increased to 24000 rpm for 2–3 minutes.
3. The thus obtained particles were left to equilibrate for at least 1 hour before being measured. The obtained mix appeared to be translucent.

In order to determine the particle size of the dispersed particles a Malvern Mastersizer X was employed. The results are set out in table 3.

TABLE 3 particle size distribution suspended carrageenan particles (cumulative mean diameters)

| Upper limit μm | no. 4 |
|---|---|
| 15.58 | 0.32 |
| 22.97 | 8.04 |
| 33.87 | 35.08 |
| 49.95 | 67.54 |
| 73.66 | 89.47 |
| 108.61 | 97.70 |
| 160.17 | 98.84 |
| 286.82 | 98.84 |
| 513.61 | 98.91 |
| 1356.26 | 100.00 |

EXAMPLE 4

A moisturizing personal care product was prepared using the following formulation (all percentages by dry weight):

2.5% spray dried kappa-carrageenan (similar to the carrageenan obtained in example 3)

3% glycerol 0.06% colouring agent 0.1% flavour 0.1% preservative (sodium methylbenzoate)

0.11% potassium chloride remainder water i) All ingredients, excluding the carrageenan, were dissolved in the water at room temperature.
ii) The carrageenan was gradually added to the resulting liquid and suspended using an T25 ultraturrax with a 18G probe, on a low speed setting.
iii) Once the suspension is complete, it was mixed at a higher shear setting for about 2 minutes to achieve a smooth texture.

The resulting product was a pourable, smooth composition with a fatty-like appearance suitable for topical application to the skin.

EXAMPLE 5

A dressing type product was prepared using the following recipe (all percentages based on dry weight):

6% co-spray dried agar/maltodextrin/xanthan mixture (ratio 1:3:0.05 respectively) maltodextrin being a 2DE maltodextrin (Paselli SA2, ex Avebe) xanthan being a food-grade xanthan ex Jungbunzlauer 4% sucrose 2.2% salt 2% flavours and spices 0.13% potassium sorbate (preservative)

remainder water i) all ingredients were dissolved at room temperature, excluding the agar-containing mixture
ii) the solution was titrated to pH 3.8 with wine vinegar
iii) the agar-containing mixture was slowly added to the aqueous composition under moderate shear using an ultraturrax T25 with 18G probe on a medium setting.
iv) once addition was complete, shear was increased to high setting for about 2 minutes.

A product was obtained which had a rheology and texture very much similar to conventional fat containing dressing type products. Furthermore, the product obtained showed good stability.

EXAMPLE 6

A similar product as in example 5 was prepared by using 7.5% co-spray dried agar/maltodextrin (ratio 1:4 respectively)

We claim:

1. A suspension of particles which comprise hydrated gelled biopolymer, said suspension being obtained by hydrating at a temperature below $T_{gel}$ dry particles of said biopolymer, said particles themselves being obtained by dehydrating a solution comprising the biopolymer at a temperature of above $T_{gel}$, the biopolymer being selected from the group consisting of agar, carrageenan, gelatin, gellan, furcelleran, alginate, (low methoxy) pectin and mixtures thereof.

2. A suspension according to claim 1 wherein the biopolymer particles have a size which is between 2 and 30 times larger than in their unhydrated state.

3. A suspension according to claim 2 wherein at least 80% by weight of the hydrated biopolymer particles has a mean size below 100 μm.

4. A suspension according to claim 3 wherein said suspension further comprises at least one member of the group consisting of a hydrocolloid and a starch based material.

5. A suspension according to claim 4 wherein the starch based material comprises maltodextrin.

6. A suspension according to claim 5 wherein the hydrocolloid comprises xanthan, guar gum, locust bean gum or modified celluloses.

7. A suspension according to claim 1 wherein further comprises flavours, fragrances, colours, vitamins, salts, sugars, sugar alcohols, emulsifiers or other water soluble adjuncts.

8. A food product or personal care product comprising a suspension according to claim 1.

9. A food product according to claim 8 which is at least partially or completely free of animal or vegetable fat.

10. A process for the preparation of a suspension of particles which comprise hydrated gelled biopolymer, said process comprising mixing dry particles of a biopolymer capable of forming a gel selected from the group consisting of agar, carrageenan, gelatin, gellan, furcelleran, alginate, (low methoxy) pectin and mixtures thereof with a liquid at a temperature lower than $T_{gel}$ of said biopolymer, said dry particles being obtained by dehydrating a solution comprising said biopolymer at a temperature above $T_{gel}$.

11. A process according to claim 10 wherein the liquid comprises water.

* * * * *